(12) United States Patent
Fishburne (10) Patent No.: US 9,084,718 B2
(45) Date of Patent: Jul. 21, 2015

(54) COMPOSITE EDENTULOUS SPACE FILLER FOR DENTAL APPLICATIONS

(71) Applicant: Cotesworth Fishburne, Rock Hill, SC (US)

(72) Inventor: Cotesworth Fishburne, Rock Hill, SC (US)

( * ) Notice: Subject to any disclaimer, the term of this patent is extended or adjusted under 35 U.S.C. 154(b) by 0 days.

(21) Appl. No.: 14/183,650

(22) Filed: Feb. 19, 2014

(65) Prior Publication Data
US 2014/0234805 A1    Aug. 21, 2014

Related U.S. Application Data

(60) Provisional application No. 61/766,396, filed on Feb. 19, 2013.

(51) Int. Cl.
| | |
|---|---|
| *A61C 3/00* | (2006.01) |
| *A61K 6/00* | (2006.01) |
| *A61C 13/15* | (2006.01) |
| *A61C 7/10* | (2006.01) |
| *A61C 13/107* | (2006.01) |
| *A61C 13/00* | (2006.01) |

(52) U.S. Cl.
CPC ............... *A61K 6/0017* (2013.01); *A61C 7/10* (2013.01); *A61C 13/0001* (2013.01); *A61C 13/0003* (2013.01); *A61C 19/003* (2013.01)

(58) Field of Classification Search
CPC ........... A61C 13/0003; A61C 13/0022; A61C 13/30; A61C 13/275; A61C 5/007
USPC .......... 433/18, 34–48, 212.1, 7, 24, 172–180; 264/17
See application file for complete search history.

(56) References Cited

U.S. PATENT DOCUMENTS

| | | | |
|---|---|---|---|
| 5,385,469 A * | 1/1995 | Weissman | 433/40 |
| 5,829,979 A * | 11/1998 | Kobashigawa et al. | 433/180 |
| 5,984,682 A * | 11/1999 | Carlson | 433/180 |
| 6,039,569 A | 3/2000 | Prasad et al. | |
| 6,854,974 B1 | 2/2005 | Suhonen | |
| 7,217,131 B2 * | 5/2007 | Vuillemot | 433/215 |
| 2006/0006561 A1 * | 1/2006 | Brajnovic | 264/17 |

* cited by examiner

*Primary Examiner* — Cris L Rodriguez
*Assistant Examiner* — Matthew Saunders
(74) *Attorney, Agent, or Firm* — B. Craig Killough; Barnwell Whaley Patterson & Helms (57) ABSTRACT

A device that is useful in forming an occupation for an edentulous space, and a method of forming the device. The device is formed by filling a tube with an ultraviolet (UV) light curable composite, and subsequently curing the light curable composite in situ. The tube is transparent, or substantially transparent, to ultraviolet (UV) light. The tube may be open at each end thereof.

14 Claims, 12 Drawing Sheets

COMPOSITE EDENTULOUS SPACE FILLER FOR DENTAL APPLICATIONS

Applicant claims the benefit of U.S. Provisional Application Ser. No. 61/766,396 filed Feb. 19, 2013.

FIELD OF THE INVENTION

This invention relates to dentistry and to dental and orthodontic devices.

BACKGROUND OF THE INVENTION

A space maintainer is a general dental or orthodontic appliance that maintains a space left by a prematurely lost tooth or a space that will be filled by a tooth not yet erupted. Space maintainers are most commonly used when a deciduous tooth, such as a deciduous molar, is prematurely lost due to decay or trauma. The space maintainer prevents teeth adjoining the space formerly occupied by the lost tooth from tilting or otherwise moving into the space, and thereby interfering with the eruption of the new tooth. Also, the adult tooth may drift, and eventually erupt in the wrong position.

Space maintainers are usually made from plastic or stainless steel. Some can be removed, while others will be cemented into the mouth. Removable space maintainers will look much like a regular retainer. It may also have artificial teeth to fill in the spaces. Usually, this type of space maintainer is used for the sake of appearance as well as to allow permanent teeth to erupt.

If a child requires a fixed space maintainer, a metal band is put around teeth adjacent to the space that needs to remain open. The dentist makes an impression of the teeth in order to create the space maintainer. The band and the models are sent to a laboratory, where the retainer is constructed. The space maintainer is cemented into the child's mouth.

Space maintainers in use include:
- A band-and-loop, wherein a stainless steel band is placed around the crown of an adjacent tooth. A loop is attached to the band, and stretched across the space, touching the other side of the open space that is preserved.
- A lingual arch, wherein bands are wrapped around teeth on both sides of the mouth, with the connecting wire often bracing against the front teeth. The lingual arch wire is typically placed on the inside, or tongue side of the mouth, or along the bottom of a crown.
- A distal shoe that is placed under the gum. If a six year molar has not erupted, this type of space maintainer may be used. Erupting teeth can be guided into position by this type of wire.

Edentulous spaces may result from extraction, trauma, anatomy, or due to dental processes, such as preparation for the installation of dental implants. Bridges or pontics may be used to fill these spaces. If several teeth are missing, a partial denture may be used. In the case of each such device discussed above, the devices are relatively expensive to construct, costing several hundreds of dollars. Further, very few dental offices can construct these devices. Therefore, they are supplied by outside vendors, such as dental laboratories, who provide the devices for installation by the dentist or orthodontist.

There is a need for inexpensive devices to fill edentulous spaces. Such devices should be capable of construction by a dentist or orthodontist using tools and materials that are readily available at dental offices.

SUMMARY OF THE INVENTION

The present invention is a device that is useful in forming an occupation for an edentulous space, and a method of forming the occupation. The device may be formed by filling a tube with an ultraviolet (UV) light curable composite or fibrous composite. The tube is transparent, or substantially transparent, to ultraviolet (UV) light. The tube may be open at each end thereof.

The composite-filled tube is positioned in an edentulous space so that the ends of the tube are adjacent to teeth that are on either side of the edentulous space. The teeth have been etched and bonded to receive and hold the composite. The tube is now squeezed, forcing composite from within the tube to spread to the teeth that are adjacent to the tube. Composite material is cured, causing the composite material to harden and occupy the edentulous space. The device and method may be manufactured and/or prepared for a relatively small amount of money, and may be installed with tools that are readily available at most dental offices and in a much shorter period of time.

DESCRIPTION OF PREFERRED EMBODIMENTS

In a preferred embodiment, a tubular member such as tube 2 is filled with dental composite resin 4. The tube may be cylindrical in shape, and have a hollow portion that receives the dental composite resin. Each end of the tube is preferred to be open.

"Composite" as used herein means a light curable composite material suitable for dental use, and includes composites that comprise fibrous materials as well as composites that do not include fibrous materials, unless otherwise stated.

The light curable composite material is preferred to be a dental composite resin 4 and is of a type that is curable with ultraviolet (UV) light. Such composites, such as direct dental composites, comprise a catalyst and an initiator. The composite material is designed to cure by polymerizing at wavelengths that are emitted by a curing light. The fully cured composite material is hard and will withstand chewing of food for an indefinite period.

The tube 2 is preferred to be formed of a material that is transparent, or substantially transparent, to wavelengths that cure the composite material, so that the dental composite resin can be cured with the tube in position. Accordingly, the UV light passes through the tube sufficiently to completely cure and harden the dental composite resin. Thus, while the tube may not be completely transparent to the UV light of the appropriate wavelength to harden the dental composite material, it should be substantially transparent so that the dental composite material is cured throughout to form the resin to be hard and durable. The tube may be cylindrical in shape, like a drinking straw, with a hollow center, or it may be formed in other geometries. The tube may be formed of polypropylene. The tube is preferred to be manually deformable, such that manually squeezing the tube filled with composite material will force a small portion of the composite material from the ends of the tube in a controllable manner.

The tube is filled with dental composite resin. The tube may be contained in a capsule, or similar device to retain the resin from escaping each end of the tube prior to use. The tube may be prepackaged in this way. The tube could be manufactured by filling a long tube with dental composite resin, and then cutting the tube to length. It is preferred that the long tube is filled under pressure to reduce the likelihood of air pockets in the dental composite resin that would negatively impact the architecture of the finished device. After the tube is filled and cut to the desired lengths, the individually cut pieces of tube filled with resin may be placed in a capsule, a black or opaque box, or similar container. The capsule or other container should be opaque to wavelengths that would tend to cure the dental composite resin prior to installation of the device. The individual lengths of the tube are preferred to be slightly longer than the longest typical application of the device and method, so that the length may be cut to the required length for the particular application. Various lengths of composite filled tubes may be supplied.

Figure 1:
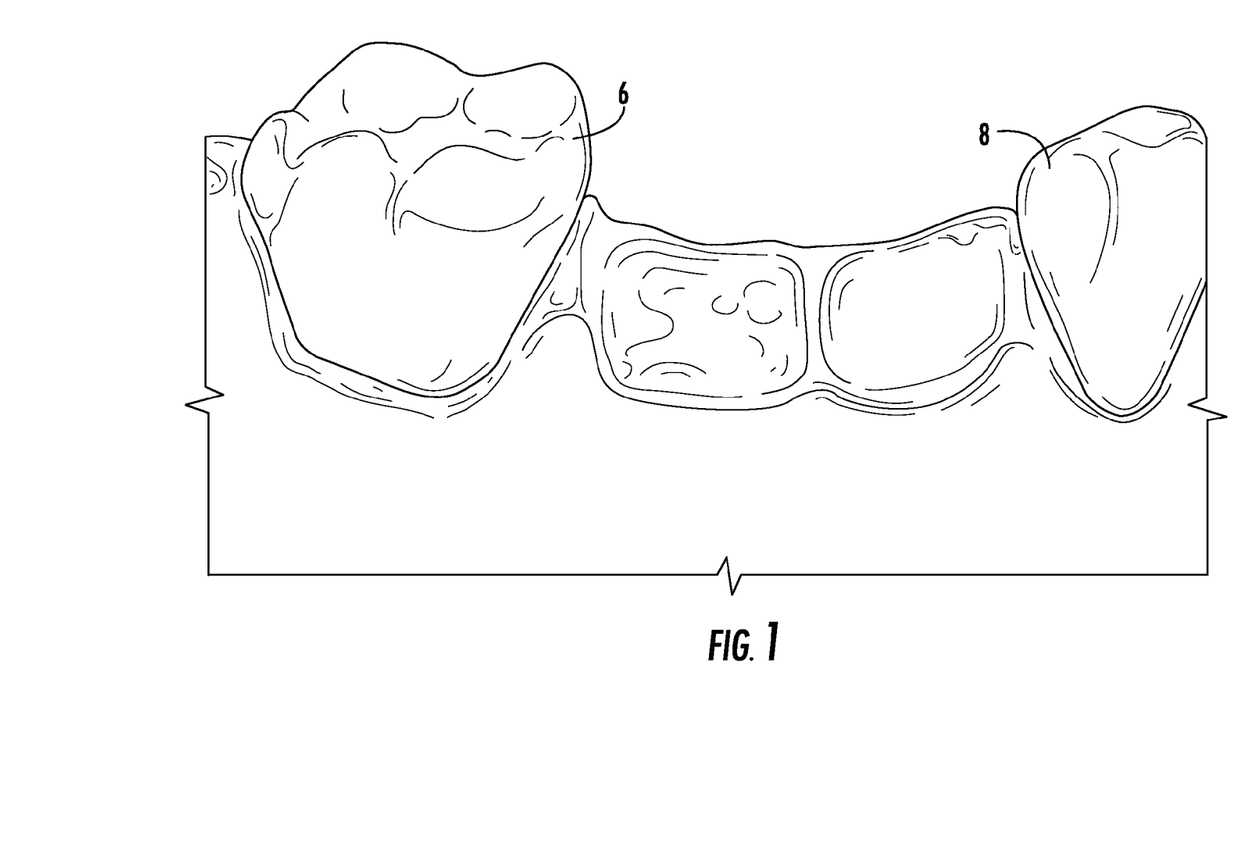
FIG. 1 shows an edentulous space between a first tooth and a second tooth.

FIG. 1 shows a first tooth 6 and a second tooth 8 adjoining an edentulous space. The edentulous space may be the result of trauma, extraction, anatomy, or other reasons that result in persons having missing teeth.

Figure 2:
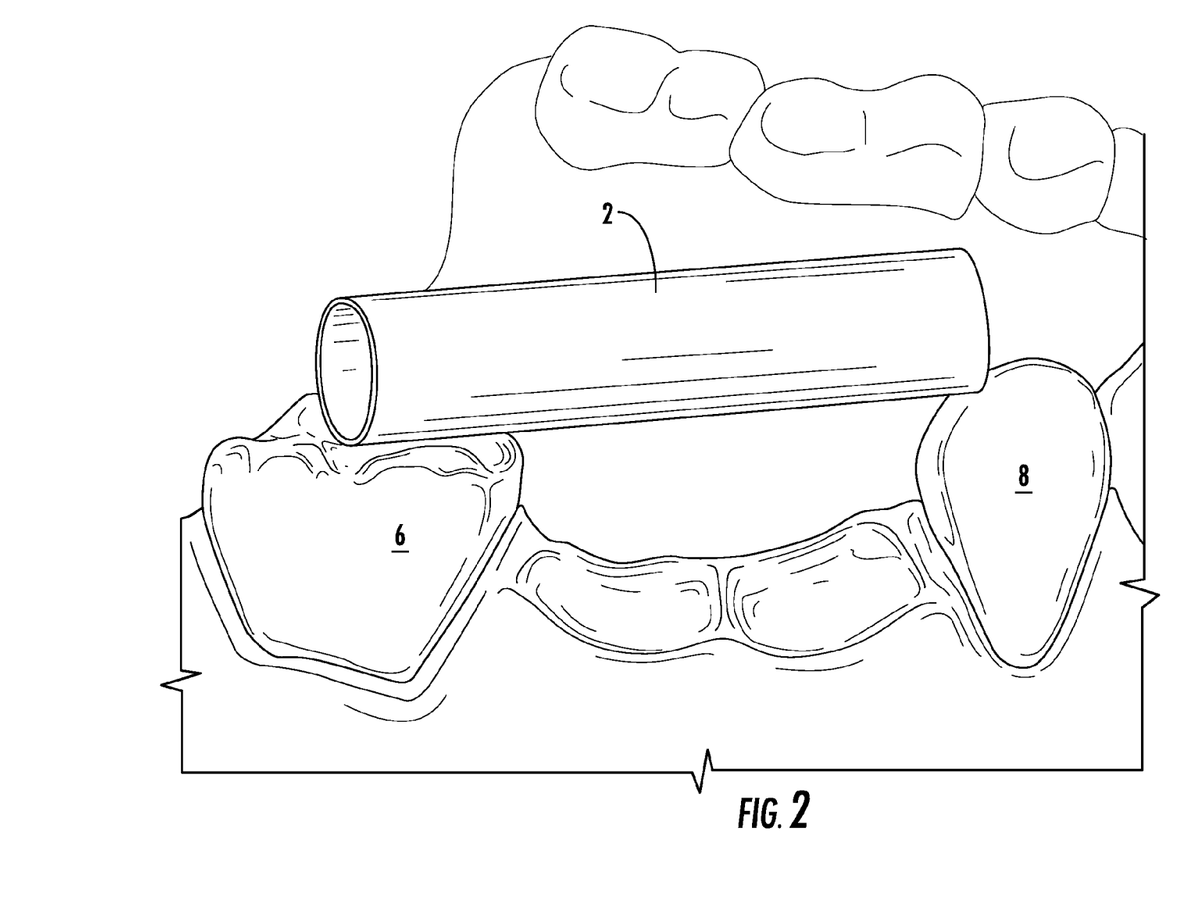
FIG. 2 shows a composite-filled tube that is longer than is required to fill the edentulous space.

FIG. 2 shows a tube according to the invention. The tube 2 is longer than the edentulous space into which it will be placed. The tube may be formed to the desired length by cutting the tube. The tube may be formed of common plastics, such as polypropylene, and may be reduced in size by cutting with scissors or similar cutters. In a preferred method, the edentulous space is measured with calipers and then cut to the length determined by the calipers to obtain a more precise measurement. Alternatively, sizing the tube may be accomplished by positioning the tube prior to cutting, and comparing the length with the length of the edentulous space, and then marking the tube and cutting the tube. The tube may be prefilled with uncured dental composite resin prior to sizing the tube. In another embodiment, the tube 2 is sized by cutting and/or trimming and then filling the tube with uncured dental resin. Various lengths of prefilled tubes may be provided for the operator to choose from. A typical tube may have a diameter of 4 to 7 millimeters.

Figure 3:
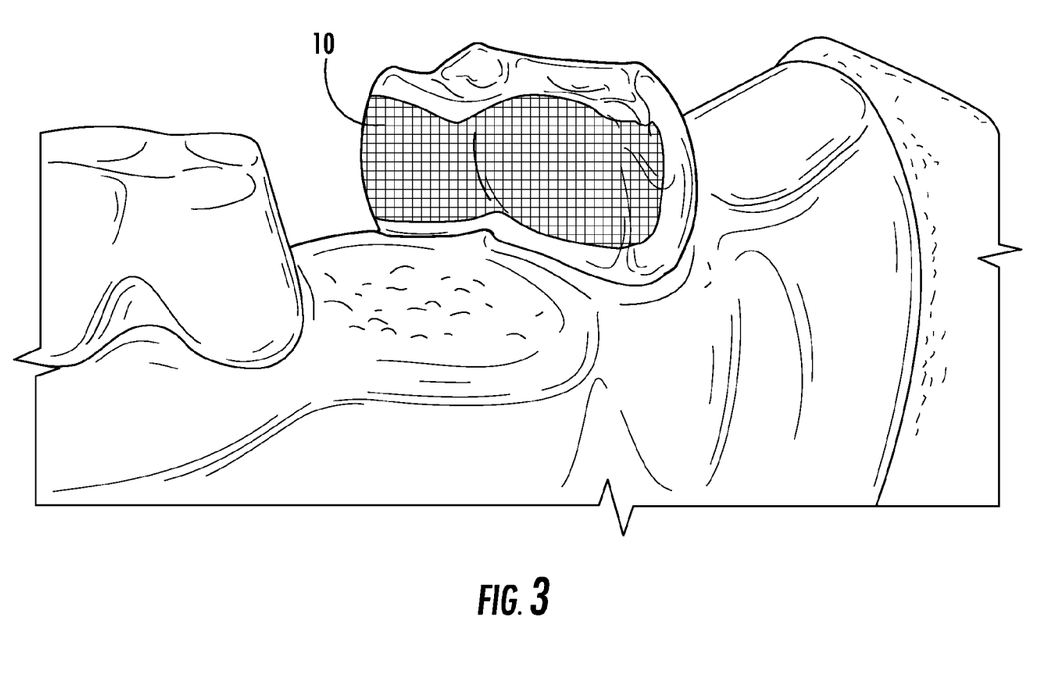
FIG. 3 demonstrates a tooth that has been etched and bonded for receiving composite material.

FIG. 3 shows a side of a tube 2 adjoining the edentulous space of proximal teeth that have been etched and bonded. Etching and bonding is a process that is known to those skilled in the art of dentistry. Etching and bonding forms a surface of the tooth that provides a strong bond with the dental composite material. The area 10 demonstrated by the hatching lines of FIG. 3 is provided for the purpose of demonstrating the surface of the tooth that is etched and bonded.

Figure 4:
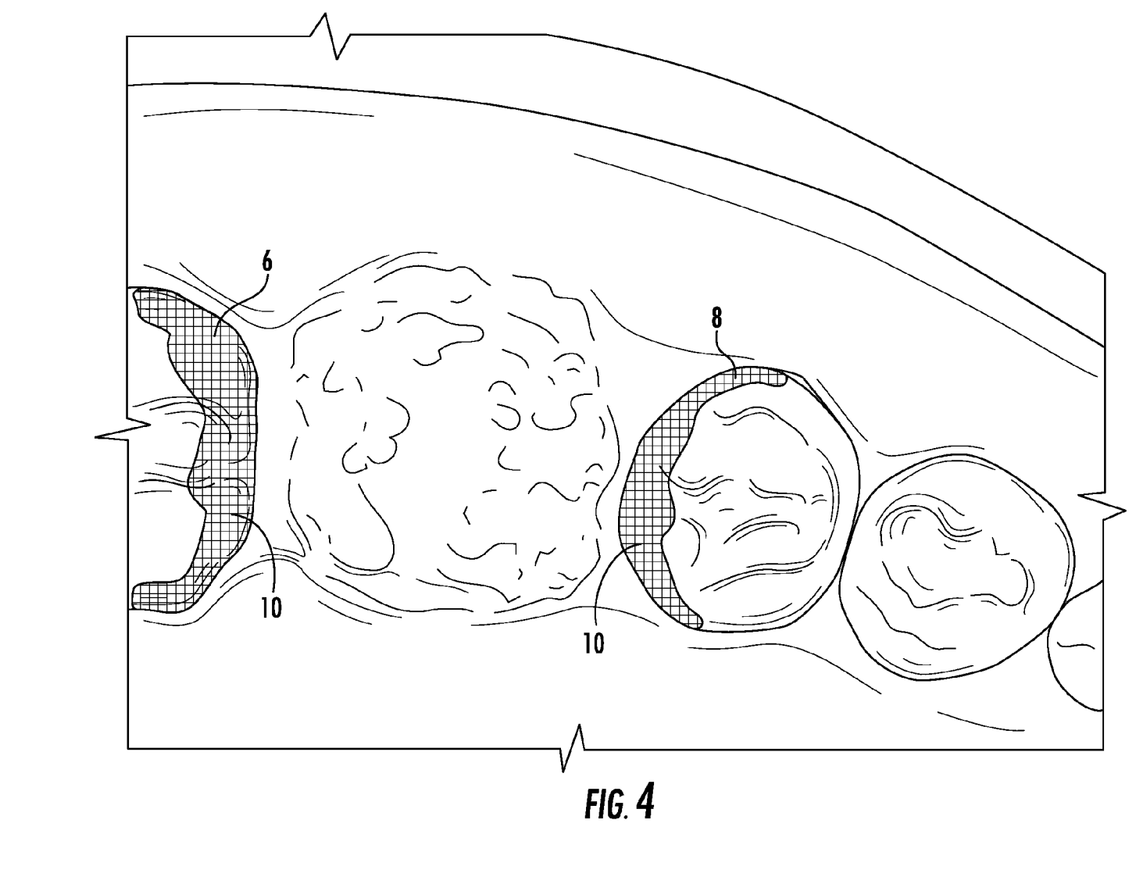
FIG. 4 shows a plan view of a first tooth and a second tooth, with the sides of the teeth that border the edentulous space being etched and bonded for receiving the composite material.

FIG. 4 shows a top plan view of the first tooth and the second tooth that adjoins the edentulous space, with the area 10 demonstrating the surface of these teeth that are etched and bonded in preparation for installation of the composite-filled tube.

Figure 5:
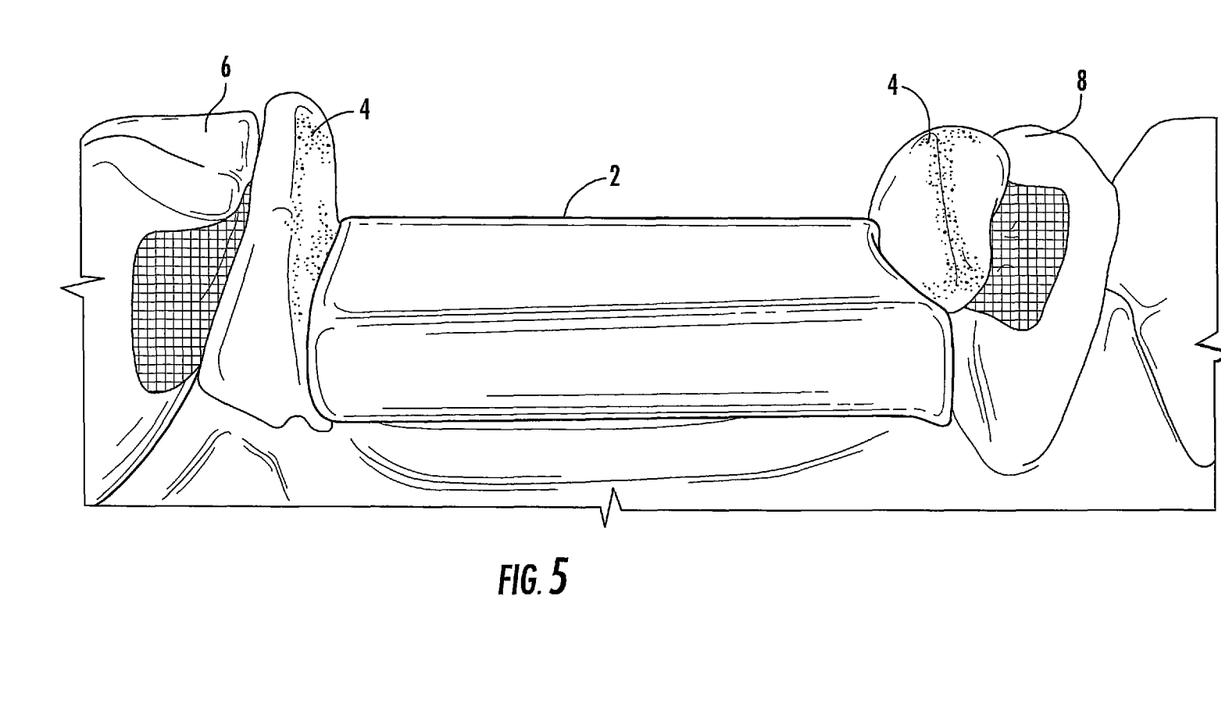
FIG. 5 demonstrates the composite-filled tube being formed to a usable length for filling the edentulous space, with composite material exiting opposite ends of the tube.

FIG. 5 demonstrates a tube 2 filled with composite material 4 that is positioned in the edentulous space and between the adjoining teeth. The tube has been squeezed, and by being open at each end, dental composite material is forced from each end of the tube so that the dental composite material contacts the first tooth 6 and the second tooth 8.

In one embodiment, a coloring agent is added to the composite to assist the operator in assuring that the composite is in contact with the teeth that adjoin the edentulous space. For teeth that cannot be readily seen due to the position in the mouth, such as a space formerly occupied by a molar, adding a blue color or other contrasting color assists is flowing the composite to occupy the edentulous space, and also makes removal of excess material easier. It may be that a very pale or stark white color may be preferable, as the ultra violet light may be blocked and prohibited from curing a dark color. In another embodiment, color is added to the composite so that the color of the composite, after curing, approximates the color of the adjoining natural teeth.

Figure 6:
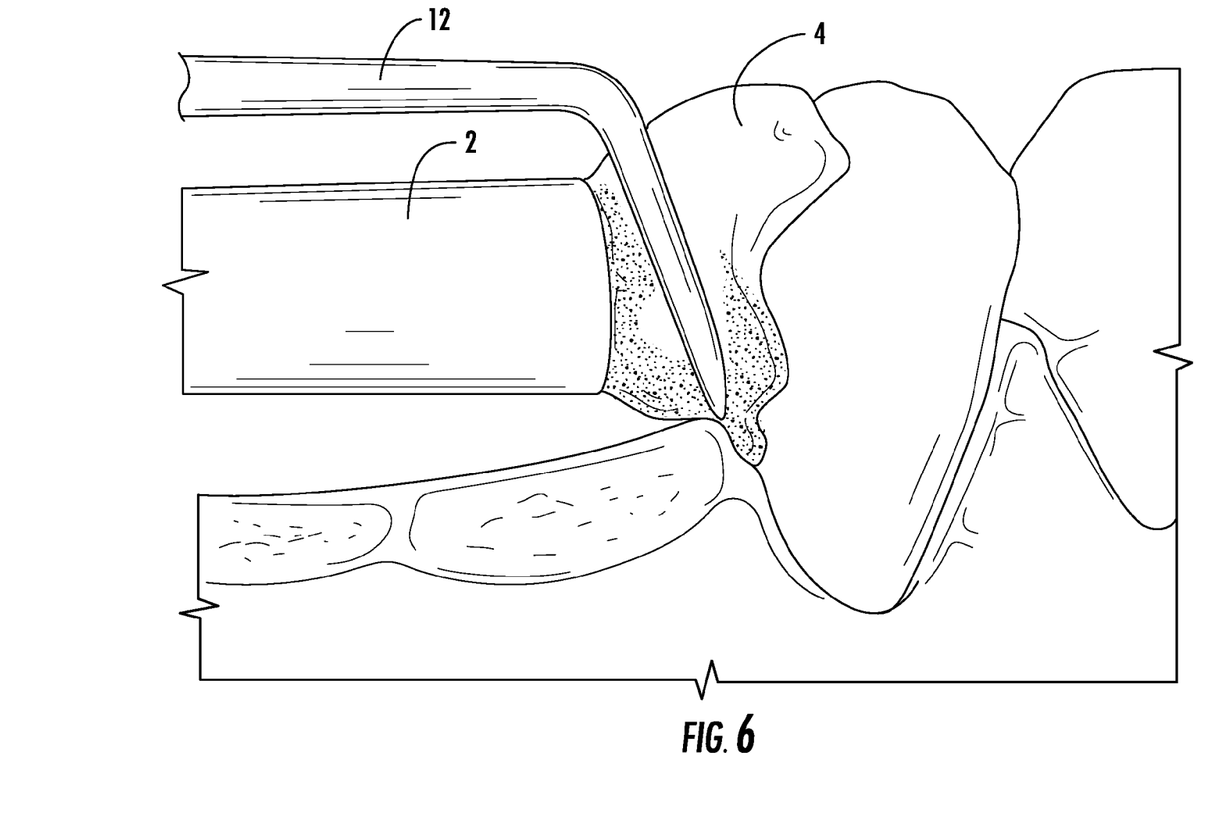
FIG. 6 demonstrates spreading and/or shaping composite material along the sides of the teeth prior to curing of the composite material.

FIG. 6 demonstrates spreading dental composite material after the tube is positioned in the edentulous space. Dental composite material that has been squeezed from each end of the tube and spread, but which may potentially interfere, or have an undesired geometry, is removed such as by a Hollenback Carver 12.

Figure 7:
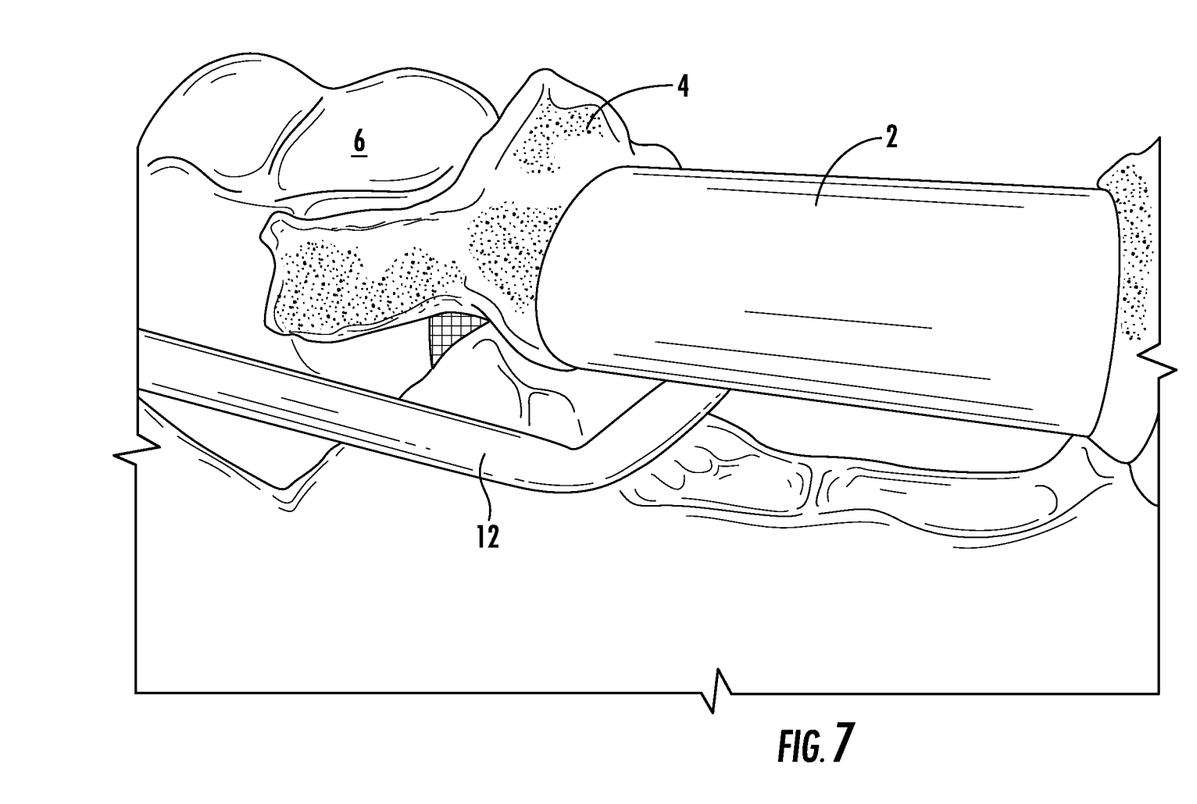
FIG. 7 is another view demonstrating spreading and/or shaping composite material along the sides of the teeth prior to curing of the composite material.

In a preferred embodiment, the dental composite material is partially cured to stabilize the composite material without completely curing it. The dental composite material may be further shaped to a desired geometry, such as by using the Hollenback Carver. See also FIG. 7.

Figure 9:
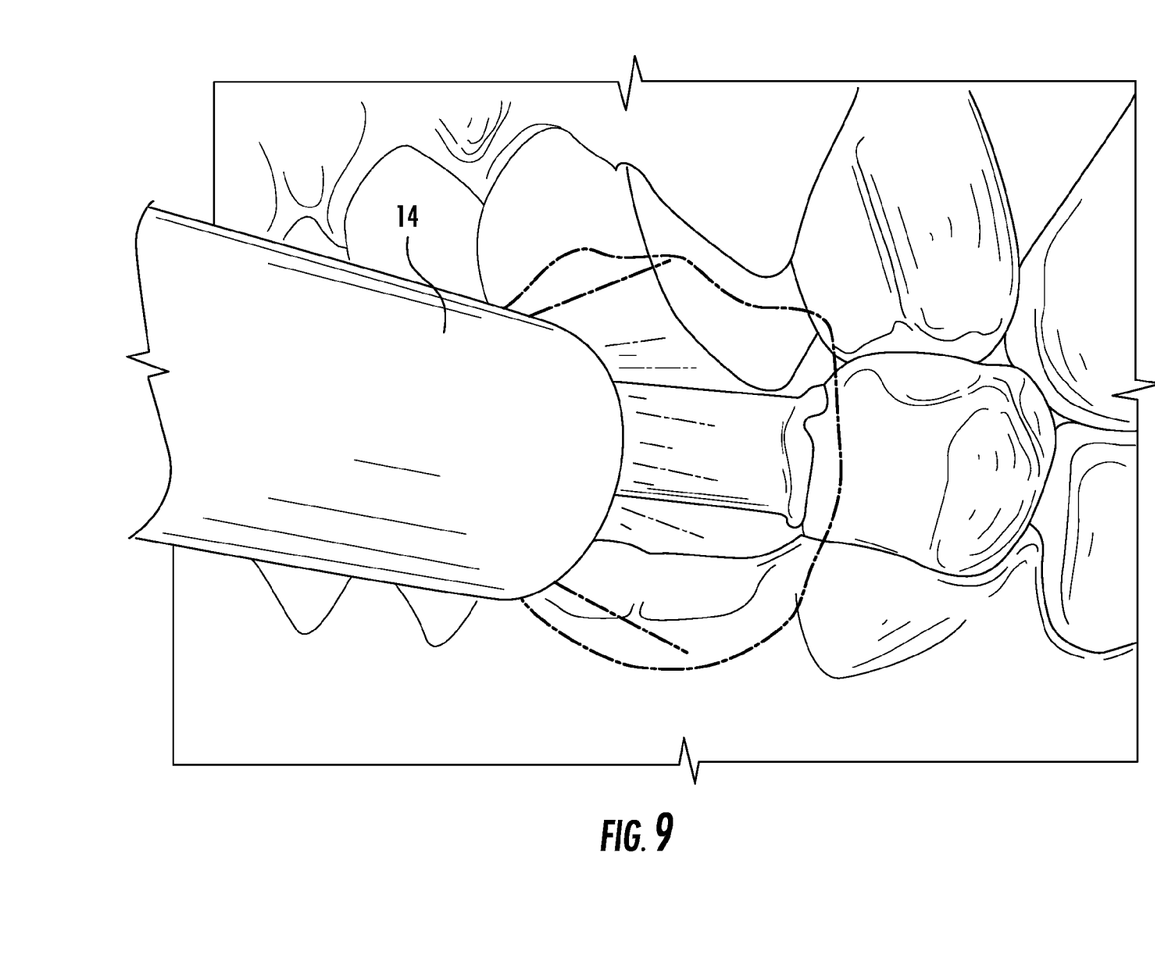
FIG. 9 demonstrates UV curing of the composite material.

FIG. 9 demonstrates curing the dental composite resin using a light emitting device 14, and the application of light of the required wavelength to the dental composite resin. The light may be ultraviolet light.

Figure 10:
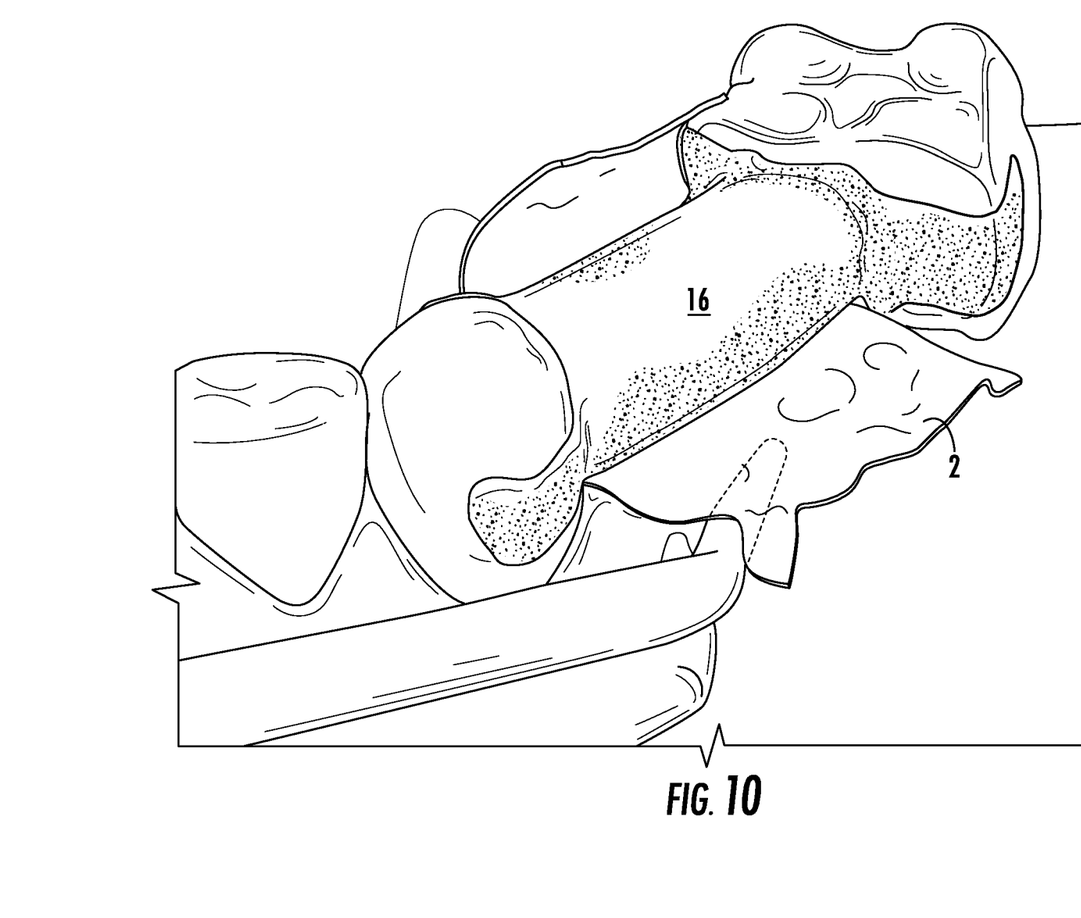
FIG. 10 shows removal of the tube after curing of the dental composite material.

After the dental composite material is completely cured and hardened by the ultraviolet light, it is preferred to remove the tube 2 that surrounds the hardened composite 16. FIG. 10. The tube may be removed by cutting the tube, such as cutting lengthwise across the top of the tube. Dental instruments such as a sharp dental scaler (for lengthwise slitting), a #35 inverted cone or rotating dental disc may be used to cut the tube. The cylinder or tube may be removed in one piece if split appropriately. In a preferred embodiment, the tube is made of plastic, such as polypropylene, and may be extracted by pulling the tube material from around the hardened composite after cutting or splitting the tube.

Figure 11:
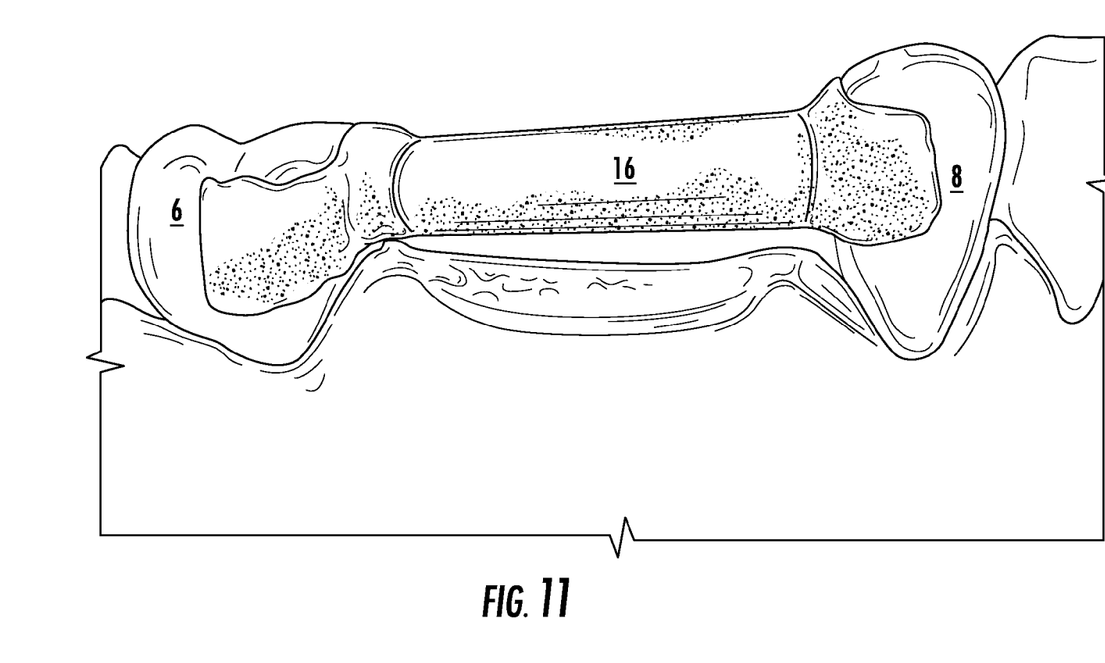
FIG. 11 shows the device in position in the edentulous space after curing, and removal of the tube.
Figure 12:
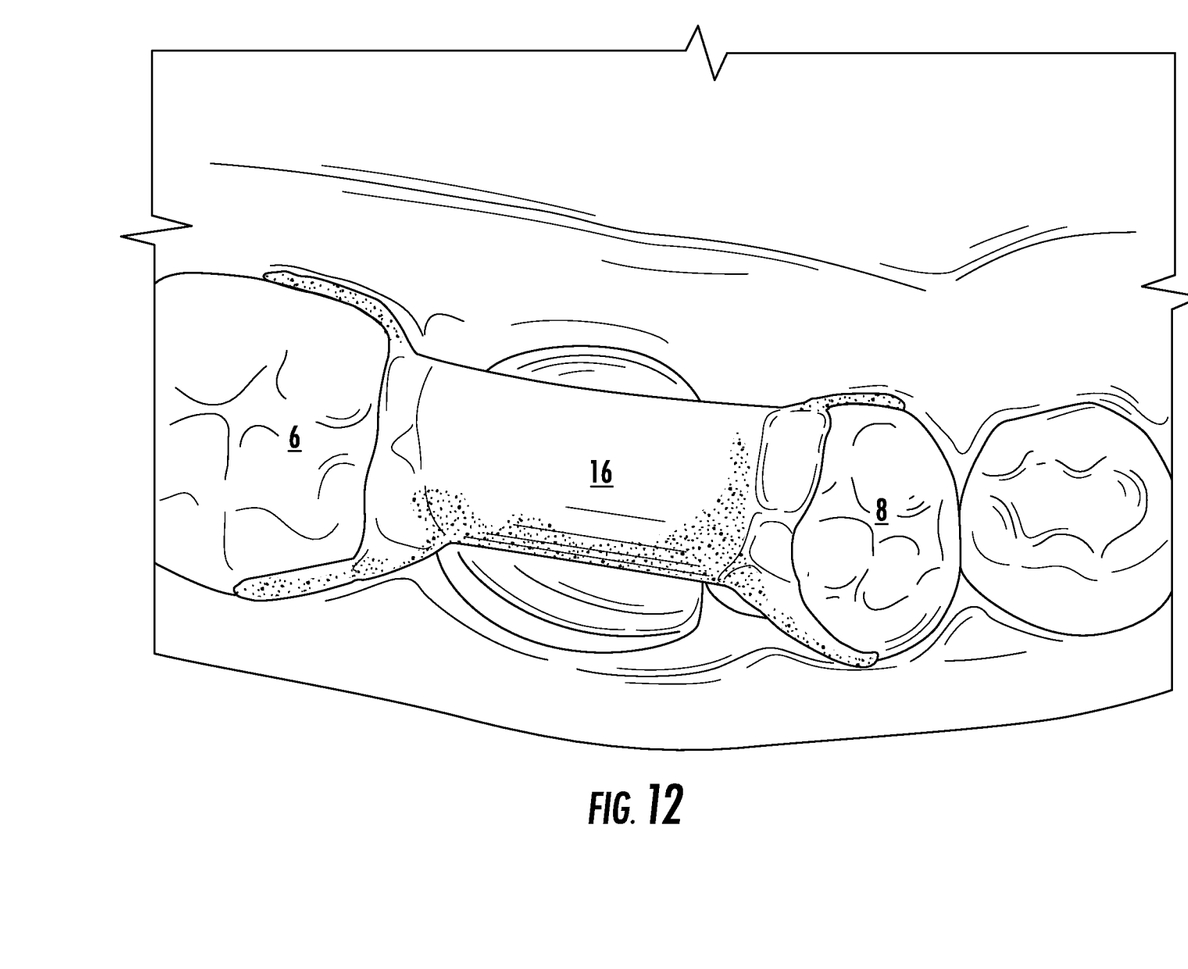
FIG. 12 is a top plan view of the device prepared according to a completed process, with the device filling the edentulous space.

FIGS. 11 and 12 show the device as completed according to the method, and occupying the edentulous space. In one embodiment, the device and method form a space maintainer. The device and method may also be used to otherwise fill edentulous spaces, or to form bridges or pontics, or to provide a temporary replacement during a dental implant procedure.

The etching and bonding as described above may be performed by first applying an acid to the areas of the teeth demonstrated in by the hatching lines in area 10 in FIGS. 3 and 4. A bonding agent is placed on these areas after the acid etches the surfaces of the teeth.

In another embodiment, a reinforcing material, such as a reinforcing bar, may be inserted longitudinally, such as coaxially, in the tube. The reinforcing bar may be surrounded by dental composite material. The reinforcing bar may the same length as, or substantially the same length as, the tube. The reinforcing bar may be formed of a substantially rigid, but strong, plastic, or it may be formed of a metal rod or wire. The reinforcing bar provides additional strength for the completed device in the event that occlusal forces are heavy, and/or the length of the device increases the moment forces to which the device is exposed. The reinforcing bar decreases the likelihood of failure of the device in some applications.

After the dental composite material is completely cured and hardened, and the tube 2 is removed, the dental composite material may be formed to a desired shape. A high speed drill as used in dental offices may be used for shaping the cured dental composite material. By way of example, the material may be used to approximate the architecture of the natural tooth that was formerly present in the edentulous space.

A bridge may be formed between two temporary crowns using the method. Relatively large proximal areas may be cut from the temporary crowns, and dental composite forced by squeezing into the voids formed by the cut out areas. The crowns may be formed of polycarbonate or stainless steel.

Figure 8A:
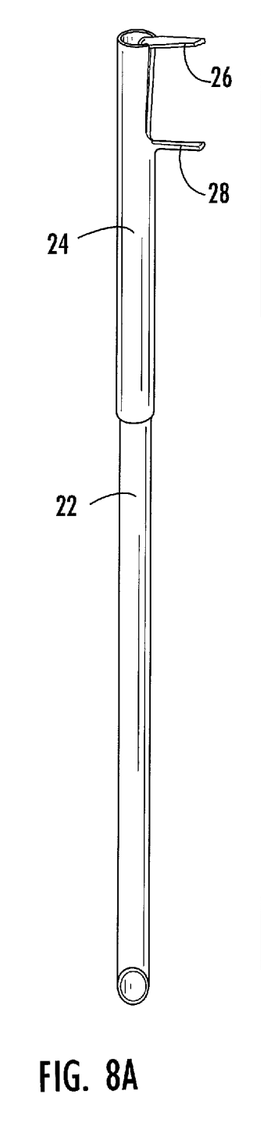
FIG. 8A shows an embodiment of a caliper that may be used to measure the edentulous space for sizing the tube filled with composite material.
Figure 8B:
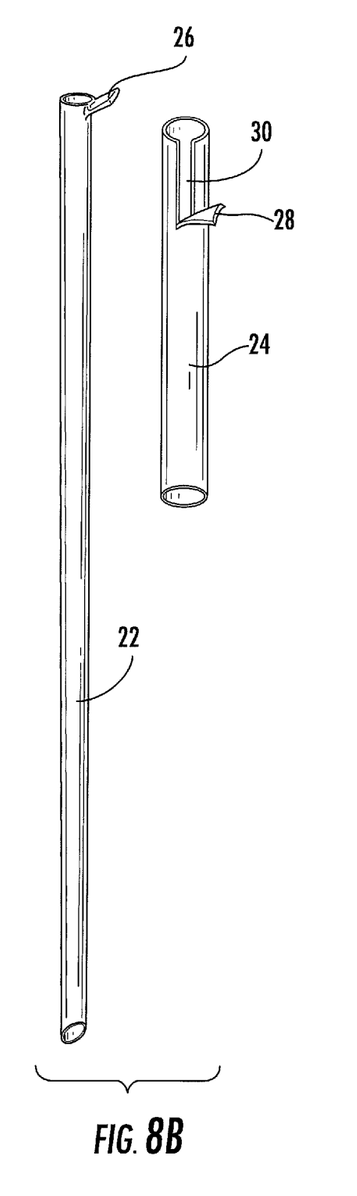
FIG. 8B shows another embodiment of a caliper that may be used to measure the edentulous space for sizing the tube filled with composite material.
Figure 8C:
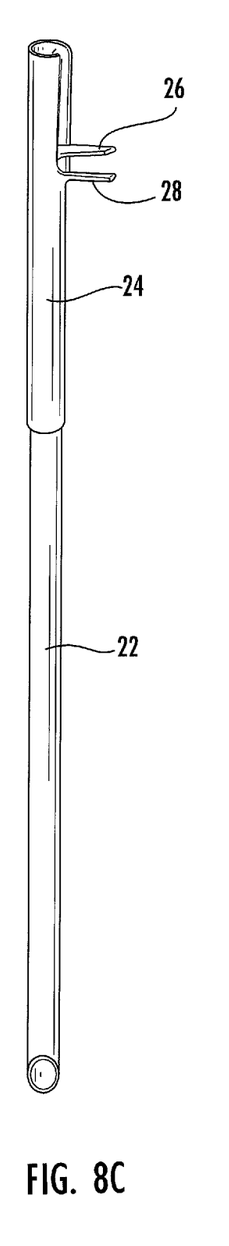
FIG. 8C shows another view of the embodiment of the caliper of FIG. 8A that may be used to measure the edentulous space for sizing the tube filled with composite material.

A caliper 20 may be used to measure the edentulous space, for sizing and cutting the tube 2. In one embodiment, a caliper may be formed of two tubes that slidably engage each other. FIGS. 8A and 8B and 8C. A first tube 22 slidably engages a second tube 24. Tube 22 has a tab 26 extending from an end thereof. Tube 22 may be longer than tube 24, and of smaller outside diameter, so as to slide within tube 24. Tube 24 receives tube 22 inside tube 24. Tube 24 has a slot 30 and a tab 28. One of the tabs may be placed against tooth 6 and the opposite tab placed against tooth 8, with the spacing of the tabs being variable by the tubes sliding relative to each other. The edentulous space may be measured with the calipers, and the tube 2 sized accordingly, such as by cutting the length of the tube.

The tubes 22, 24 may be formed of metal, such as stainless steel or brass. The tabs, 26, 28, and slot 30 may be formed by known methods of working metal.

What is claimed is:

1. A method of producing a device for filling an edentulous space, comprising the steps of:
    filling a tubular member with a light curable composite material, wherein the tubular member is closed along its length;
    forming the tubular member to a length that fits within the edentulous space;
    positioning the tubular member in the edentulous space with a first open end of the tubular member positioned adjacent to a first tooth on one side of the edentulous space and positioning a second open end of the tubular member adjacent to a second tooth on an opposite side of the edentulous space;
    causing light curable composite material to be emitted from the first open end of the tubular member and causing the light curable composite material emitted from the first open end of the tubular member to contact the first tooth, and causing light curable composite material to be emitted from the second open end of the tubular member and causing the light curable composite material emitted from the second open end of the tubular member to contact the second tooth; and
    exposing the tubular member and the light curable composite material to a light having a wavelength that hardens the light curable composite material until the light curable composite material is hardened and bonded to the first tooth and the second tooth.

2. The method of claim 1, wherein the tubular member is open on a first end and is open on a second, opposite end, and wherein the light curable composite material is exposed on the first end and the second, opposite end of the tubular member.

3. The method of claim 1, further comprising a step of squeezing the tubular member, forcing light curable composite material emitted from the first open end of the tubular member to contact the first tooth and forcing light curable composite material emitted from the second open end of the tubular member to contact the second tooth.

4. The method of claim 1, further comprising steps of etching a first tooth on a first side of the edentulous space and etching a second tooth on a second side of the edentulous space prior to positioning tubular member in the edentulous space.

5. The method of claim 1, further comprising a step of forming the tubular member to an approximate length of the edentulous space prior to filling the tubular member with light curable composite material, and subsequently forming the tubular material to the desired length after filling the tubular member with light curable composite material.

6. The method of claim 1, further comprising a step of squeezing the tubular member, forcing light curable composite from the first open end of the tubular member to contact the first tooth and forcing light curable composite material from the second open end of the tubular member to contact the second tooth, and subsequently removing excess light curable composite material from the first tooth prior to exposing the tubular member and the light curable composite material to the light having the wavelength that hardens the light curable composite material.

7. The method of claim 1, wherein the tubular member permits light having the wavelength that hardens the light curable composite material to pass through walls of the tubular member.

8. The method of claim 1, wherein the tubular member is transparent to light having the wavelength that hardens the light curable composite material.

9. The method of claim 1, further comprising a step of removing the tubular member from the light curable composite material after hardening of the light curable composite material.

10. The method of claim 1, wherein the light that hardens the light curable composite material is ultraviolet light.

11. The method of claim 1, further comprising a step of placing the tubular member in a container for transporting the tubular member after filling the tubular member with the light curable composite material.

12. The method of claim 1, further comprising steps of exposing the tubular member and the light curable composite material to the light having the wavelength that hardens the light curable composite material until the light curable composite material is partially cured, forming the partially cured composite material within the edentulous space, and subsequently exposing the tubular member and the light curable composite material to the light having the wavelength that hardens the light curable composite material until the light curable composite material is further hardened.

13. The method of claim 1, further comprising steps of etching a first tooth on a first side of the edentulous space and etching a second tooth on a second side of the edentulous space prior to positioning tubular member in the edentulous space, and placing a bonding agent on an etched surface of the first tooth and the second tooth.

14. The method of claim 1, further comprising a step of positioning a rigid reinforcing member in the tubular member prior to exposing the tubular member and the light curable composite material to the light having the wavelength that hardens the light curable composite material.

* * * * *